(12) United States Patent
Schulthess

(10) Patent No.: US 8,079,255 B2
(45) Date of Patent: Dec. 20, 2011

(54) YARN TESTING APPARATUS

(75) Inventor: Jürg Schulthess, Uster (CH)

(73) Assignee: Uster Technologies AG, Uster (CH)

( * ) Notice: Subject to any disclaimer, the term of this patent is extended or adjusted under 35 U.S.C. 154(b) by 652 days.

(21) Appl. No.: 11/997,328

(22) PCT Filed: Jul. 21, 2006

(86) PCT No.: PCT/CH2006/000382
§ 371 (c)(1),
(2), (4) Date: Mar. 6, 2008

(87) PCT Pub. No.: WO2007/014475
PCT Pub. Date: Feb. 8, 2007

(65) Prior Publication Data
US 2008/0209998 A1    Sep. 4, 2008

(30) Foreign Application Priority Data
Jul. 30, 2005 (CH) .................................. 1273/05

(51) Int. Cl.
*G01L 5/04* (2006.01)
(52) U.S. Cl. .......................................................... 73/159
(58) Field of Classification Search .................... 73/159, 73/160
See application file for complete search history.

(56) References Cited

U.S. PATENT DOCUMENTS

| | | | | |
|---|---|---|---|---|
| 2,144,767 A | * | 1/1939 | McCallum | 242/615.3 |
| 3,960,593 A | * | 6/1976 | Heusser | 134/37 |
| 4,970,402 A | * | 11/1990 | de Vuyst et al. | 250/559.12 |
| 5,313,775 A | * | 5/1994 | Binder et al. | 57/280 |
| 5,701,729 A | * | 12/1997 | Rees et al. | 57/3 |
| 6,842,244 B2 | * | 1/2005 | Bedard et al. | 356/338 |

FOREIGN PATENT DOCUMENTS

JP        03143874 A  *  6/1991

* cited by examiner

*Primary Examiner* — Hezron E Williams
*Assistant Examiner* — Tamiko D Bellamy
(74) *Attorney, Agent, or Firm* — Luedeka, Neely & Graham, P.C.

(57) ABSTRACT

The device is used for the automatic determination of characteristics on textile test material such as yarns, rovings, and slivers. A path is provided for the test material, through which path the test material is moved in its longitudinal direction. At least one measuring element for measuring a parameter of the test material is arranged along the path. In order to reduce the depositing of loose fibers, dust, or dirt particles, a plurality of suction elements, which are arranged along the path and spaced apart from one another, are provided and generate a vacuum, by means of which the undesired particles are sucked from the path.

12 Claims, 6 Drawing Sheets

YARN TESTING APPARATUS

This application claims priority under any and all applicable statutes, acts, treaties, and agreements on international application PCT/CH2006/000382 filed Jul. 21, 2006 and Swiss application 01273/05 filed Jul. 30, 2005.

TECHNICAL AREA

The invention relates to a device for the automatic determination of characteristics on textile test material such as yarns, rovings and slivers, according to the preamble of the first claim. The invention also relates to a method for removing undesired particles such as loose fibres, dirt or dust from a device for the automatic determination of characteristics on textile test material such as yarns, rovings and slivers, according to the preamble of the further independent claim.

PRIOR ART

Such a device is known from CH-671'105, with which measurement variations of yarns, rovings or slivers can be continuously measured, for example, while a feed mechanism moves the yarn, roving or sliver in its longitudinal direction through a measuring element. Upstream and/or downstream from the measuring element, guide means are provided in a known manner, which guide the test material in such a way that during its movement in the longitudinal direction through the measuring element, as far as possible it does not carry out any lateral deflections, or, in other words, as far as possible does not oscillate.

A disadvantage of devices of this type is that undesired particles such as loose fibres, dust and dirt are deposited at certain points of the measuring element arranged in a fixed manner and of the fixed guide means. Such particles are entrained by the test material or released by the test material. This applies all the more, the higher the speed with which the test material is moved and the narrower a measuring channel or a measuring gap in the measuring element. As the dust, the dirt and the loose fibres are deposited precisely where no contact takes place from the running test material, these deposits are generally found at certain outstanding points next to the path of the test material. Such points satisfy certain conditions, so the deposits can build up undisturbed. The deposits impair the function of the measuring element, in particular when this is an optical measuring element. However, they can also impede the movement of mechanical parts, for example pulleys or guide rollers, or block the path of the test material.

CH-563'021 A5 deals with the undesired depositing of foreign materials on the measuring capacitor itself. It proposes to guide an air flow over the top of the measuring capacitor in order to prevent the depositing. The air flow is generated by generating an excess pressure in the interior of the apparatus housing by means of a ventilator. Above the measuring capacitor, the apparatus housing has a slot, through which air flows out and blows fibre flyaway from the measuring capacitor. As an alternative, the air can be guided through a guide channel from the apparatus housing and be blown out along the front side of the apparatus. Blowing air out of the apparatus housing has the disadvantage that the foreign materials that are blown away reach the surroundings in an uncontrolled manner and are possibly deposited at other sites, where they could also be disruptive. Moreover, the heat from the apparatus housing is warmer than the ambient air because of the heat emitted from electrical components in the housing. This additional heat may influence the generally very sensitive measuring element and lead to incorrect measurements.

EP-0'467'159 A1 sets itself the object of cleaning a spinning machine. For this purpose, suction tubes are arranged in the region of the drafting arrangement and the air vortex nozzle, which suction tubes suck off non-spun fibre fly.

DESCRIPTION OF THE INVENTION

A device of the type mentioned, which does not have the drawbacks mentioned and which reduces the depositing of loose fibres and dust and dirt particles, is now to be proposed by the invention. Furthermore, a corresponding method for removing undesired particles, such as loose fibres, dirt or dust from a device for the automatic determination of characteristics on textile test material is to be disclosed.

This and other objects are achieved by the device and the method as defined in the independent claims. Advantageous embodiments are disclosed in the dependent claims.

At least one point along a path or a track, which the test material traverses, the invention provides means for removing undesired particles, which originate from the test material itself or which are entrained by the test material. The means for removing undesired particles contain a plurality of suction elements, which are arranged along the path and spaced apart from one another and are suitable for generating a vacuum, by means of which the undesired particles can be sucked from the path.

At least one subset of suction elements is preferably to be configured and arranged in such a way that an air flow, which engages the test material, can be built up in the path. The measuring channel and the suction elements are to be matched to one another in such a way that the air flow, in at least one portion of the measuring channel, flows over the channel wall of the measuring channel. The suction elements may, viewed in the movement direction of the test material, be arranged at a plurality of points upstream from the drive device. Such devices for removal are particularly effective when they are arranged in the region of a measuring element or in the regions of the supply device of the test material. As an alternative to this, depending on the type of measuring element, it may be advantageous to arrange the suction elements outside the region of a measuring element.

In a preferred embodiment, provided along the path is a substantially U-shaped measuring channel, in which at least one measuring element and the means for removing undesired particles are arranged. The latter contain an air channel, which extends along the path and in which openings configured as suction elements are arranged. Alternatively, at least one suction element may be configured as at least one tubular piece with an opening, which is aligned with a zone in the region of the path. A suction element may also be configured as a ventilator, which generates an air flow directed toward it around the test material and the measuring element.

The advantages achieved by the invention are in particular that the feed mechanism can move the test material at a substantially higher speed through the measuring element and the guides, without significant deposits of dirt being formed. Such a speed may be, for example, 800 m/min and substantially exceed the previously conventional values of 400 m/min. It is therefore now also possible to better exploit the performance of the electronics present, which further process the signals from the measuring element, for example by comparing and classifying periodically occurring measured values with limit values, and to shorten the measuring times. A further advantage is that the device according to the invention in this manner also contributes to keeping the workplace in a textile laboratory clean.

LIST OF DRAWINGS

The invention will be described hereinafter with the aid of an embodiment and with reference to the accompanying drawings, in which.

IMPLEMENTATION OF THE INVENTION

Figure 1:
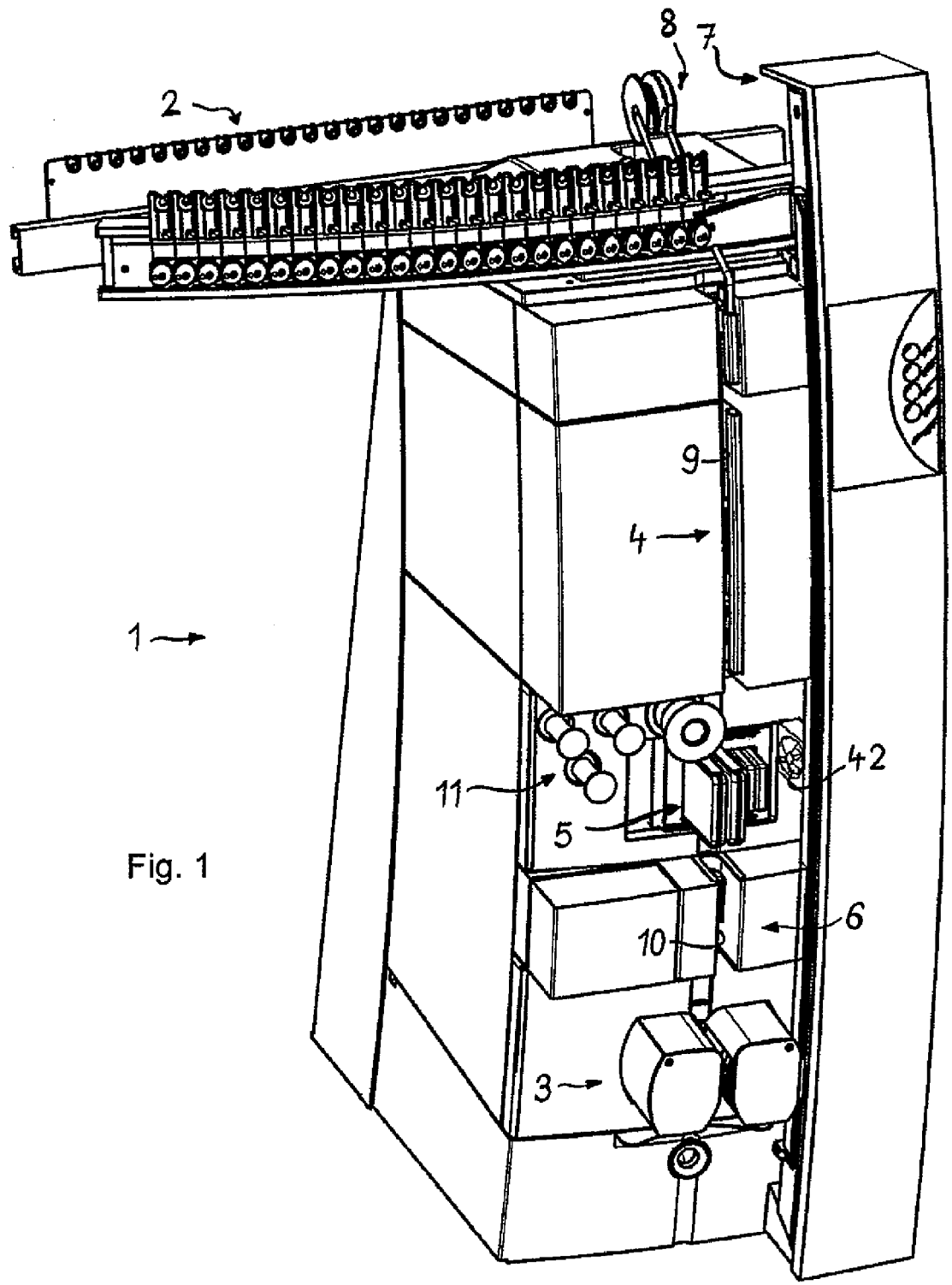
FIG. 1 shows a perspective view of a yarn testing apparatus.

FIG. 1 shows a device 1 according to the invention for the automatic determination of characteristics on textile test material such as yarns, rovings and slivers, which is also designated in brief as a yarn testing apparatus. This device 1 has, in a manner known per se, a supply device 2, a feed mechanism 3, a plurality of measuring elements 4, 5, 6 here and an insertion device 7 for the automatic insertion of the test material into the measuring elements 4, 5, 6. A test material is not shown here but a path 8 for the test material, which is formed by the elements arranged one behind the other such as the supply device 2, measuring elements 4, 5, 6 and feed mechanism 3, may be seen. A substantially V-shaped measuring channel 9 and 10 is also to be seen in the regions of the measuring elements 4 and 6. In the region of the measuring element 5, which is configured here as a measuring capacitor for a capacitive measurement, for example the mass of the test material, a group 11 is also seen, consisting of pulleys, which are suitable to guide a fibre sliver, for example, laterally into the path 8 in order to test the fibre sliver in the measuring element 5 and/or 6.

Figure 2:
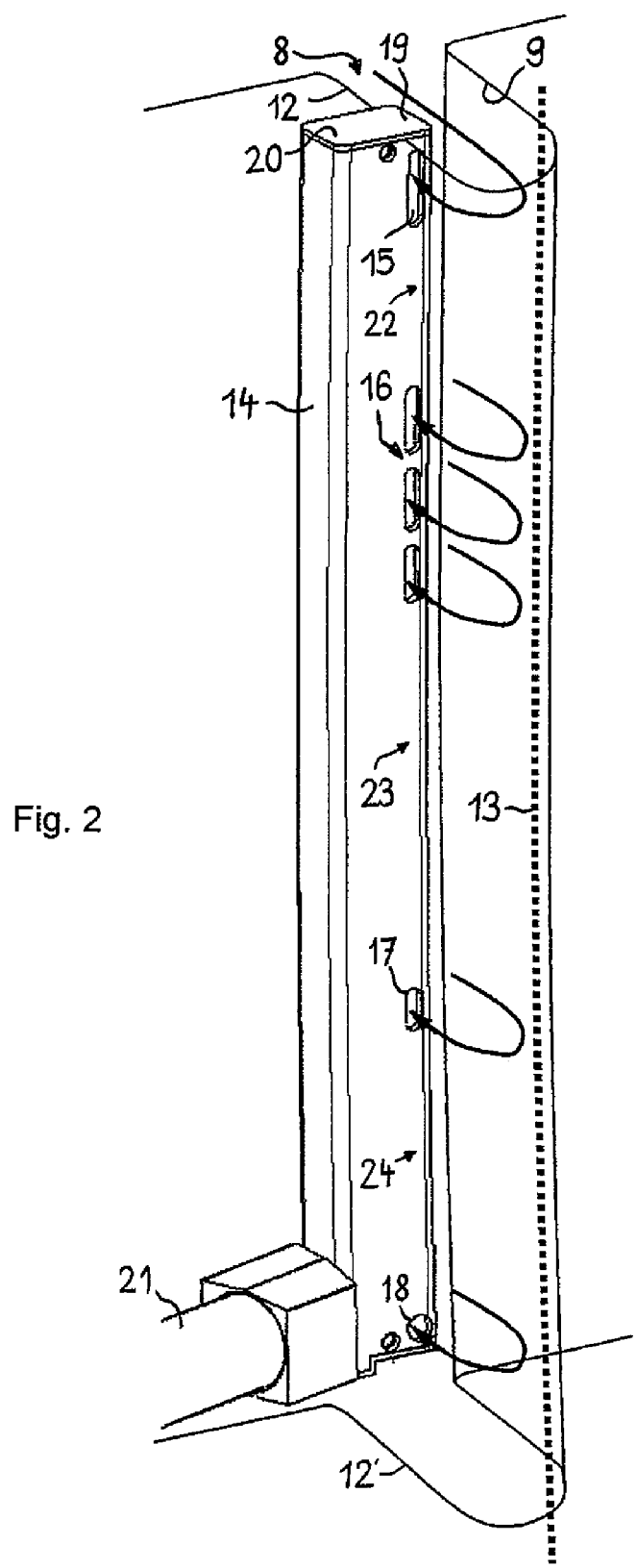
FIG. 2 shows a perspective view of a measuring channel.

FIG. 2 shows the path 8 in the region of the measuring channel 9 as it appears viewed from the interior of the device 1 (which is practically not possible). The measuring channel 9 is therefore shown in a transparent manner here. Its V-shaped cross-section can be seen at its upper and lower limitations 12, 12'. A dashed line marks a test material 13, a yarn, for example, here. An air channel 14 is let laterally into the measuring channel 9 with the limitation 12 in such a way that it projects with a part 19 into the measuring channel 9 and with a part 20 into the interior of the device 1. The air channel 14 is connected at the bottom, for example, to a line 21, which is in turn connected to a suction pump, known per se and not shown here. Openings 15, 16, 17 and 18 are arranged at spacings 22, 23 and 24 from one another. The spacings 22, 23, 24 can be adapted to the position of the individual measuring elements (not shown in FIG. 2). Depending on the type of measuring element, it may be advantageous to provide the openings 16, 17 in the region of a measuring element. On the other hand, there are measuring elements, the function of which can be impaired by an air flow; in this case, the openings 15, 18 are preferably provided outside the region of the measuring element. The air channel 14 with its openings 15, 16, 17 and 18 forms means here for removing undesired particles, these particles being sucked off.

Figure 3:
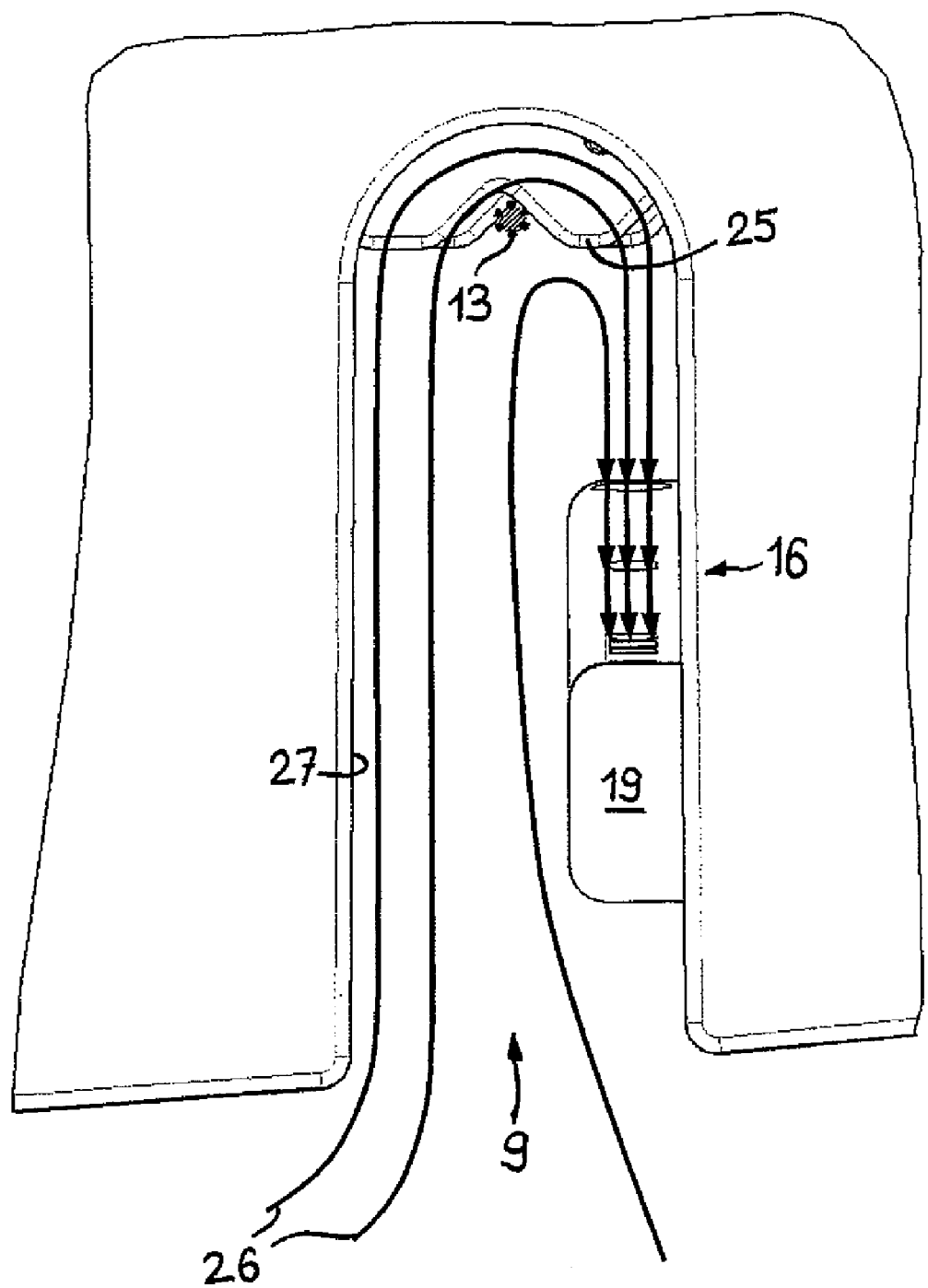
FIG. 3 shows a cross-section through the measuring channel according to FIG. 2.

FIG. 3 shows a cross-section through the measuring channel 9 above the opening 16. A measuring element 25, which projects into the measuring channel 9, and the test material 13 in section, are seen here at about the level of the openings 16. Also visible is the part 19 of the air channel 14 projecting into the measuring channel 9. The air flow in the measuring channel 9, which flows over the channel wall 27, engages the test material 13 and the measuring element 25 and then enters the openings 16, is shown by arrows 26.

Figure 4:
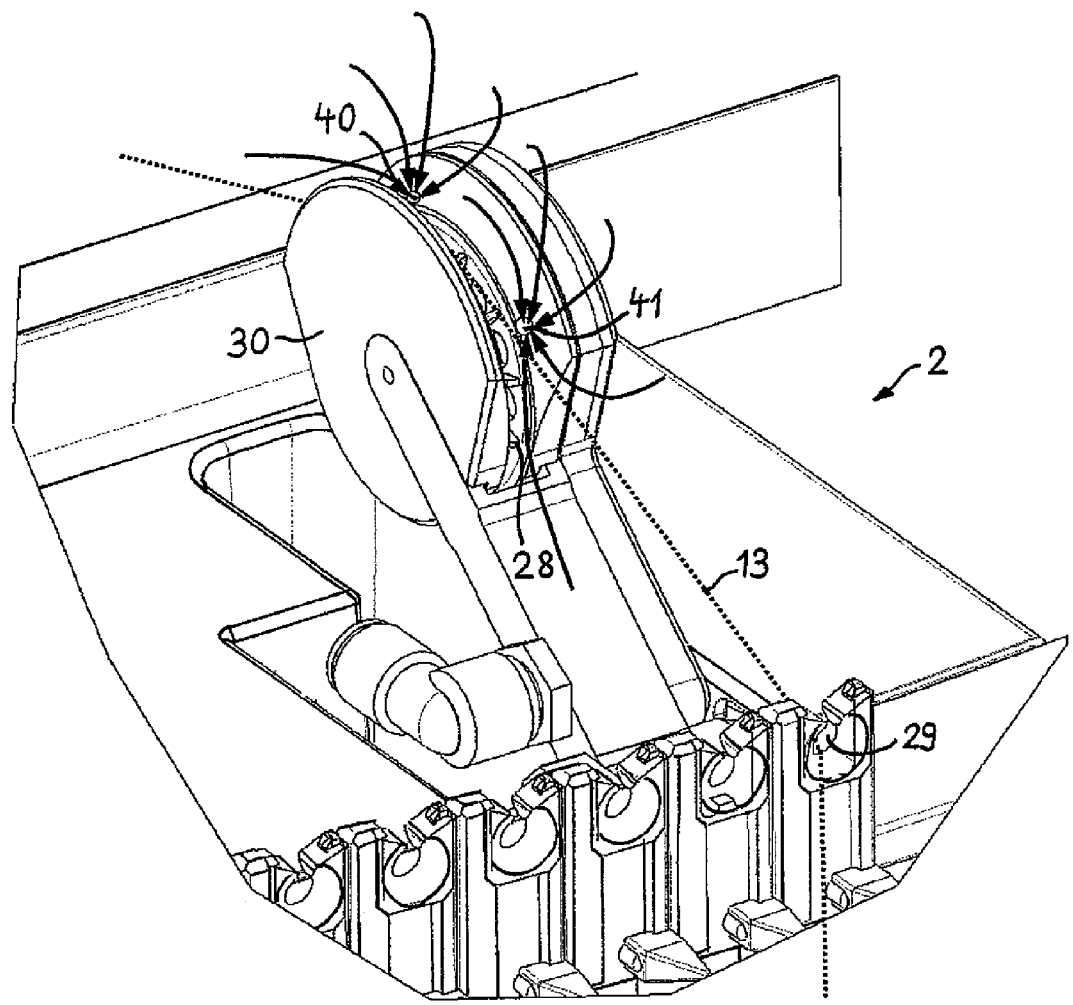
FIG. 4 shows a perspective view of a supply device.

FIG. 4 shows a part of the supply device 2 for the test material 13 with a deflection pulley 28, which can be partially seen, which guides supplied test material 13 into an eyelet 29, which is aligned with the measuring channel 9, deflects the test material and therefore, with the measuring channel 9, forms a part of the path 8 for the test material. The deflection pulley 28 can rotate freely and is mounted in a bracket arm 30. Provided here as means for removing undesired particles are openings 40 and 41, which are connected to a vacuum source (not shown in FIG. 4).

Figure 5:
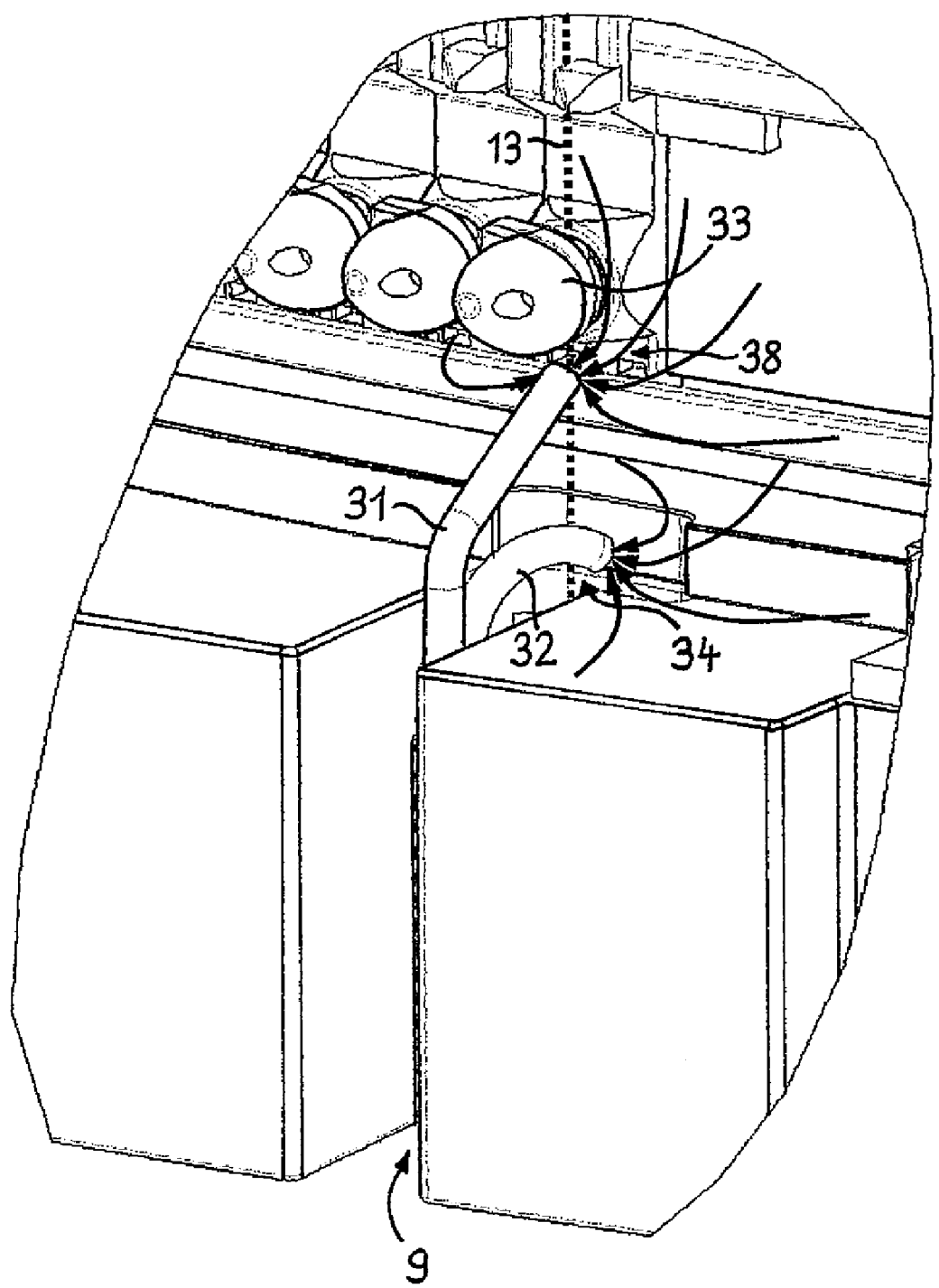
FIG. 5 shows a perspective view of an entry to the measuring channel.

FIG. 5 shows a further portion of the path 8 before entry of the test material 13 into the measuring channel 9. Two tubular pieces 31, 32, the openings of which act upon the surroundings of a clamp 33 for the test material 13 and the entry 34 to the measuring channel 9, are provided here as means for removing undesired particles. The clamp 33 is part of the supply device 2. It is open during the measurements on the test material 13 and therefore does not clamp the test material 13. The clamp 33 is used while changing from one test material to another test material.

Figure 6:
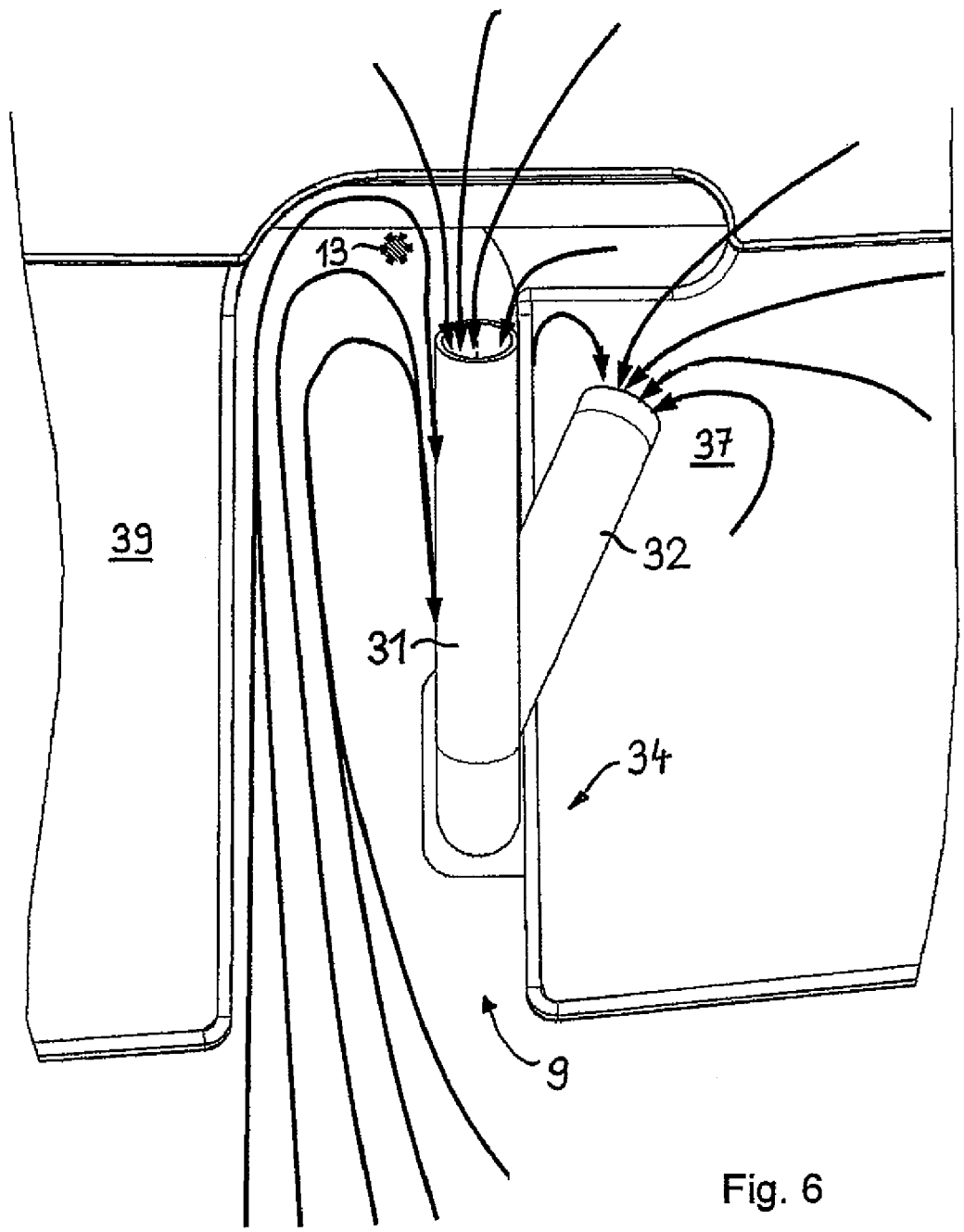
FIG. 6 shows a plan view of the entry to the measuring channel.

FIG. 6 shows a plan view of the entry 34 to the measuring channel 9 with the test material 13 in cross-section. It is seen here that the second tubular piece 32 with its end is aligned in such a way that it acts upon the entry 34 with its horizontal face 37. The first tubular piece 31, on the other hand, is aligned with a region 38 (see FIG. 5) at the exit of the clamp 33. The tubular pieces 31, 32 may be fastened, for example, to the air channel 14 and also connected via the air channel 14 to a vacuum source.

The mode of action of the device 1 according to the invention is to be described below. When the test material 13 is inserted by the insertion device 7 in a manner known per se into the device 1 according to the invention, it extends over the deflection pulley 28, the measuring channels 9 and 10, the measuring element 5 and the feed mechanism 3. The measurements on the test material 13 can then begin and the measuring elements 4, 5, 6 present may measure parameters, for example, such as mass, diameter, hairiness, foreign material content, etc., on the running test material 13. The test material 13 is pulled along the path 8 by the feed mechanism 3, with it being moved via the deflection pulley 28 through the eyelet 29 and through the various measuring elements 4, 5, 6 in its longitudinal direction. Deposits of dust, dirt or loose fibres can already settle in the bracket arm 30 and in the deflection pulley 28 and are also partially caused by the deflection pulley 28. The openings 40, 41, for example, continuously suck off such deposits and this results in no deposits being conveyed further, either, by the test material 13 itself, from the bracket arm 30 with the deflection pulley 28. During the subsequent passage of the test material 13 through the fixed eyelet 29, the test material 13 rubs on it and there is the possibility of dirt or fibre parts being released there from the test material 13 and then being deposited further down at the entry 34 to the measuring channel 9. Such deposits from the horizontal faces 37, 39 and from the surroundings of the clamp 33 are now engaged there by the air flow, which enters the tubular pieces 31, 32. In the subsequent measuring channel 9, openings 15 to 18 bring about cleaning of the measuring channel 9. Spacings 22, 23, 24 between the openings 15 to 18 are adapted to the measuring elements 4 arranged along this measuring channel 9. It can thus be assumed that each of these measuring elements 4 records or measures a specific parameter of the test material 13. Measuring elements 4 of this type can form constrictions in the cross-section of the measuring channel 9, as is indicated, for example, in FIG. 3 with the measuring element 25, which projects into the measuring channel 9. As, owing to its movement in its longitudinal direction along the path 8 and the measuring channel 9, the test material 13 can oscillate, transverse movements of the test material 13 may also be produced. In the regions of such restrictions, there is therefore an elevated risk of deposits forming when the test material 13 touches the measuring element 25, for example. Therefore, the openings 16, 17, are also preferably arranged particularly in such regions in order to avoid loose fibres being entrained by the test material 13, for example, and being deposited further down in the path 8. As this is nevertheless still possible, further openings 18 are also provided further down.

As can be seen from FIGS. 2 and 3, the deposits are to be guided in a controlled air flow 26, for example, along the channel wall 27 into the openings 15 to 18. For this purpose, the air channel 14 with the measuring channel 9 and the openings 15 to 18 should be matched to one another in such a way that the air flow 26 in at least one channel portion flows over the entire channel wall 27 of the measuring channel 9 and discharges into the openings 15 to 18. In any case, the device according to the invention should continuously remove loose particles so they no longer deposit later at undesired points along the path. Dust, which should continuously be removed, forms through friction with the running yarn 13 in particular in regions of yarn guides, which are in turn arranged in the direct vicinity of the measuring elements.

As can be seen from FIG. 1, a suction element for sucking off undesired particles can also be configured as a ventilator 42. The ventilator 42 is provided at a suitable point, next to the measuring elements 5 here, and sucks air from the surroundings. The undesired particles are thus removed.

The measuring channel 9, 10 may also have other forms apart from the particularly favourable U-shape if these are suitable for receiving measuring elements and favour an air flow of the type which allows the undesired particles to be removed as effectively as possible. It is also advantageous to gradually reduce the number of openings for the air along the path in the movement direction of the yarn. The density of the openings in a first part of the path should therefore be greater than toward its end. This takes account of the circumstance that less and less undesired particles occur with increasing distance from the supply device.

The invention claimed is:

1. A device for automatic determination of characteristics on textile test material, the device comprising:
   a path through which the test material is movable in its longitudinal direction,
   at least one measuring element arranged along the path for measuring a parameter of the textile test material,
   a feed mechanism for generating a longitudinal movement of the test material in the path,
   a supply device for supplying the test material into the path, and
   means for removing undesired particles, where measuring the parameter does not include any measurement of the undesired particles,
   wherein the means for removing undesired particles contain a plurality of suction elements that are arranged along the path and spaced apart from one another and are suitable to generate a vacuum, by means of which the undesired particles are suckable from the path.

2. The device according to claim 1, wherein at least one subset of suction elements is configured and arranged in such a way that an air flow, which engages the test material, can be built up in the path.

3. The device according to claim 2, wherein a measuring channel bounded at least in part by a channel wall and comprising at least one measuring element is provided along the path and the subset of suction elements and the measuring channel are matched to one another in such a way that the air flow in at least one channel portion flows over an entirety of the channel wall in the at least one channel portion.

4. The device according to claim 1, wherein the means for removing undesired particles contain a flow channel extending along the path, in which flow channel a plurality of openings configured as the suction elements are arranged.

5. The device according to claim 1, wherein at least one of the suction elements is configured as at least one tubular piece with an opening that is aligned with a zone in a region of the path.

6. The device according to claim 1, wherein at least one of the suction elements is arranged in a region of a measuring element.

7. The device according to claim 1, wherein at least one of the suction elements is arranged outside a region of a measuring element.

8. The device according to claim 1, wherein at least one of the suction elements is arranged in a region of the supply device of the test material.

9. The device according to claim 1, wherein at least one of the suction elements is configured as a ventilator.

10. A method for removing undesired particles from a device for automatic determination of characteristics on textile test material, in which device the test material is moved along a path in its longitudinal direction and a parameter of the test material is measured, wherein a vacuum, by means of which the undesired particles are sucked from the path, is generated at a plurality of points, which are spaced apart from one another, along the path.

11. The method according to claim 10, wherein an air flow, which engages the test material, is built up in the path.

12. The method according to claim 11, wherein a measuring channel bounded at least in part by a channel wall and comprising at least one measuring element is provided along the path and the air flow flows over an entirety of the channel wall in at least one channel portion.

* * * * *